(12) United States Patent
Andrus et al.

(10) Patent No.: US 8,768,435 B2
(45) Date of Patent: Jul. 1, 2014

(54) FOREIGN BODY LOCATION AND RETRIEVAL DEVICE

(75) Inventors: Charles Hiram Andrus, St. Louis, MO (US); Patrick Christopher Andrus, St. Louis, MO (US); Virginia E. Foster, St. Louis, MO (US); Krishi Peddada, Cupertino, CA (US)

(73) Assignee: Saint Louis University, St. Louis, MO (US)

( * ) Notice: Subject to any disclaimer, the term of this patent is extended or adjusted under 35 U.S.C. 154(b) by 30 days.

(21) Appl. No.: 13/605,086

(22) Filed: Sep. 6, 2012

(65) Prior Publication Data

US 2013/0245421 A1 Sep. 19, 2013

Related U.S. Application Data

(60) Provisional application No. 61/531,975, filed on Sep. 7, 2011.

(51) Int. Cl.
*A61B 5/05* (2006.01)
*A61B 8/14* (2006.01)
*B66C 1/42* (2006.01)

(52) U.S. Cl.
USPC ........... 600/424; 600/409; 600/459; 294/86.4

(58) Field of Classification Search
USPC ......... 600/104, 153, 154, 409, 437, 439, 424, 600/459, 567; 294/86.4; 606/1, 170, 205
See application file for complete search history.

(56) References Cited

U.S. PATENT DOCUMENTS

| | | | |
|---|---|---|---|
| 3,836,776 A | 9/1974 | Gullekson et al. | |
| 4,976,723 A | 12/1990 | Schad | |
| 5,176,702 A | 1/1993 | Bales et al. | |
| 5,275,166 A | 1/1994 | Vaitekunas et al. | |
| 5,395,033 A | 3/1995 | Byrne et al. | |
| 5,496,347 A | 3/1996 | Hashiguchi et al. | |
| 5,749,889 A | 5/1998 | Bacich et al. | |
| 5,849,022 A | 12/1998 | Sakashita et al. | |
| 5,961,441 A | 10/1999 | Plumb et al. | |
| 6,017,353 A | 1/2000 | Rankins | |
| 6,077,280 A | 6/2000 | Fossum | |
| 6,206,904 B1 | 3/2001 | Ouchi | |
| 6,663,654 B1 | 12/2003 | Husain | |
| 6,802,846 B2 | 10/2004 | Hauschild et al. | |
| 7,169,167 B2 | 1/2007 | Chu | |
| 7,947,039 B2 | 5/2011 | Sartor | |
| 8,062,246 B2 | 11/2011 | Moutafis et al. | |
| 8,075,478 B2 | 12/2011 | Campos | |
| 8,083,765 B2 | 12/2011 | Lee et al. | |
| 2007/0197895 A1 | 8/2007 | Nycz et al. | |
| 2008/0228072 A1 | 9/2008 | Nycz et al. | |
| 2010/0160731 A1 | 6/2010 | Giovannini et al. | |
| 2010/0179587 A1 | 7/2010 | Grant et al. | |
| 2010/0312141 A1 | 12/2010 | Keast et al. | |

OTHER PUBLICATIONS

International Search Report, PCT/US2012/053890, dated Oct. 26, 2012, pp. 10.

*Primary Examiner* — Michael Rozanski
(74) *Attorney, Agent, or Firm* — Armstrong Teasdale LLP

(57) ABSTRACT

Devices having the capability to both locate and retrieve objects are disclosed. More particularly, the present disclosure relates to devices having a probe comprising an ultrasound detector for locating and a grasper for retrieving objects from a medium. The present disclosure further relates to devices having a probe comprising an electromagnetic detector for locating and a grasper for retrieving metallic objects from a medium. Devices of the present disclosure are specifically adapted for use as medical devices for locating and retrieving a foreign body in a subject in need.

20 Claims, 15 Drawing Sheets

FOREIGN BODY LOCATION AND RETRIEVAL DEVICE

CROSS-REFERENCE TO RELATED APPLICATIONS

This application claims priority to provisional patent application No. 61/531,975, filed on Sep. 7, 2011, which is incorporated herein by reference in its entirety.

BACKGROUND OF THE DISCLOSURE

The present disclosure relates generally to instruments for locating and retrieving objects. More particularly, the present disclosure relates to devices having a probe including an ultrasound detector and a grasper for locating and retrieving objects from a medium. The present disclosure further relates to devices having a probe including an electromagnetic detector and a grasper for locating and retrieving metallic objects from a medium.

Objects that are not visible to the eye present significant difficulties in their location and retrieval. One specific example is when foreign objects made from materials such as metal, wood, plastic, and glass become lodged in tissue. Medical professionals must locate and remove these objects to prevent further complications such as infection, toxicity and further tissue damage. Foreign objects may be located and removed by exploratory surgery in which a medical professional follows the presumed path of a foreign object as it traveled through the patient's tissue. Exploratory surgery often involves static pre-surgery two-dimensional x-rays, external ultrasound, CAT scan images, and other types of pre-surgery imaging to locate the foreign object. Pre-surgery imaging suffers from drawbacks such as providing the exact location and/or depth of the foreign object within the tissue.

Loss of an object within a medium such as a dark or cloudy liquid presents another example where the object may need to be located and retrieved. For example, fasteners such as bolts and screws may be dropped in containers of oil and paint. Location and retrieval of these objects may require reaching into the medium and feeling around for the object, which can be messy and undesirable as well as require additional time to clean up afterward.

Although medical professionals may be well-equipped with the latest scanning equipment, no tool is presently available that both determines the location of a foreign body near the tool and provides a way to remove the foreign body in real time as the patient remains upon an operating table during surgery. The general population could also benefit from a tool that both determines the location of an object and provides a way to retrieve the object once it is located. Accordingly, there exists a need for the development of a tool that allows for both determining in real time the three-dimensional location of an object and providing a way to retrieve an object that is hidden from view.

SUMMARY OF THE DISCLOSURE

The present disclosure relates generally to devices for locating and retrieving objects. More particularly, the present disclosure relates to devices that can both locate and retrieve objects that are hidden from view.

In one aspect, the present disclosure is directed to a device for locating and retrieving an object in a medium. The device comprises a probe comprising an ultrasound detector; and a probe tip, wherein the ultrasound detector is positioned proximate to the probe tip; and a grasper slidably coupled to the probe and comprising: a movable portion; and a non-movable portion coupled to the movable portion and comprising a grasper tip; wherein the probe tip and the grasper tip are configured to grasp the object therebetween.

In another aspect, the present disclosure is directed to a device for locating and retrieving a metallic object. The device comprises a probe comprising an electromagnetic detector; and a probe tip, wherein the electromagnetic detector is positioned proximate to the probe tip; and a grasper slidably coupled to the probe and comprising: a movable portion; and a non-movable portion coupled to the movable portion and comprising a grasper tip; wherein the probe tip and the grasper tip are configured to grasp the metallic object therebetween.

In yet another aspect, the present disclosure is directed to a medical device for locating and retrieving a foreign body in a subject in need thereof. The medical devices comprise a detector; and a probe tip, wherein the detector is positioned proximate to the probe tip; and a grasper slidably coupled to the probe and comprising: a movable portion; and a non-movable portion coupled to the movable portion and comprising a grasper tip; wherein the probe tip and the grasper tip are configured to grasp the foreign body therebetween.

BRIEF DESCRIPTION OF THE DRAWINGS

The disclosure will be better understood, and features, aspects and advantages other than those set forth above will become apparent when consideration is given to the following detailed description thereof. Such detailed description makes reference to the following drawings, wherein.

Figure 1:
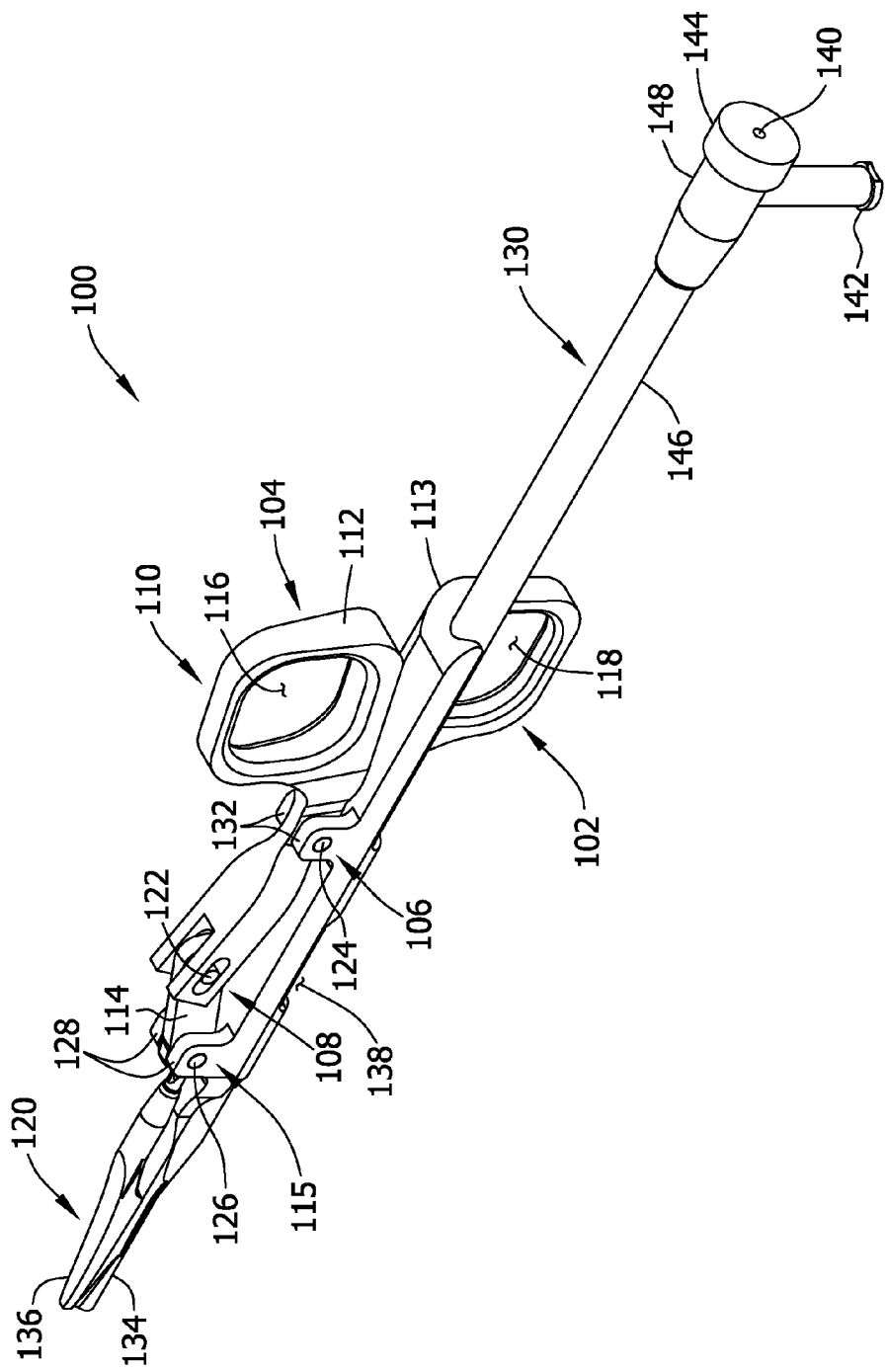
FIG. 1 is an illustration depicting a perspective view of a device for locating and retrieving an object according to one embodiment of the present disclosure.

While the disclosure is susceptible to various modifications and alternative forms, specific embodiments thereof have been shown by way of example in the drawings and are herein described below in detail. It should be understood, however, that the description of specific embodiments is not intended to limit the disclosure to cover all modifications, equivalents and alternatives falling within the spirit and scope of the disclosure as defined by the appended claims.

DETAILED DESCRIPTION

Unless defined otherwise, all technical and scientific terms used herein have the same meaning as commonly understood by one of ordinary skill in the art to which the disclosure belongs. Although any methods and materials similar to or equivalent to those described herein may be used in the practice or testing of the present disclosure, the preferred materials and methods are described below.

In accordance with the present disclosure, devices have been developed that allow for both locating and retrieving an object in a medium. More particularly, the present disclosure is directed to devices for both locating and retrieving an object in a medium. In one aspect, the present disclosure is directed to a device having a probe using an ultrasound detector for locating an object and a grasper for retrieving the object. In another aspect, the present disclosure is directed to a device having a probe using an electromagnetic detector for locating a metallic object and a grasper for retrieving the metallic object. In yet another aspect, the present disclosure is directed to a medical device for locating and retrieving a foreign body in a subject in need thereof. The devices of the present disclosure serve as handheld devices that the user grips and holds while having the capability of indicating the presence and location of an object in a medium while in use.

In one aspect, the present disclosure is directed to a device for both locating and retrieving an object. The device includes a probe using an ultrasound detector for locating an object and a grasper for retrieving the object. One particularly suitable embodiment includes a surgical device having a probe using an ultrasound detector for locating an object and a grasper for retrieving the object. A particularly suitable ultrasound detector is a small ultrasound that images at the proximate tip in a 360 degree horizontal direction or a linear array in a vertical direction. Because the ultrasound detector is directional, the direction of the object in relation to the ultrasound detector may be determined and allow for movement of the probe and device in the direction of the object. Suitable ultrasound detectors may be commercially available catheter ultrasound probes (e.g., Olympus Corp.; Center Valley, Pa. and Fujinon Corp.; Tokyo, Japan).

In another aspect, the present disclosure is directed to a device for both locating and retrieving an object. The device includes a probe using an electromagnetic detector for locating a metallic object and a grasper for retrieving the metallic object. One particularly suitable embodiment includes a surgical device having a probe using an electromagnetic detector for locating a metallic object and a grasper for retrieving the metallic object. The electromagnetic detector includes magnetically sensitive elements that alter a voltage potential when in the presence of a metallic object. The electromagnetic detector may be, for example, an inductive coil and an electronic sensor. The electromagnetic detector is electronically coupled to an electrical circuit that may include multiple oscillating sub-circuits, which may further include transistors, resistors, capacitors, filters, processors and combinations thereof. The oscillating sub-circuits transmit current through the device at specific frequencies. The processor interprets differences in frequencies generated by oscillating sub-circuits and provides output to a display interface. Because the electromagnetic detector functions by inductance, the inductance changes as the electromagnetic detector is moved relative to the metallic object. The electrical components provide a varying signal through the wiring to a display interface options as described herein to notify the user when an object is located.

In yet another aspect, the present disclosure is directed to a medical device for locating and retrieving a foreign body in a subject in need thereof. In one embodiment the device includes a probe housing an ultrasound detector for locating a foreign body and a grasper for retrieving the foreign body. In another embodiment, the medical device includes a probe housing an electromagnetic detector for locating a metallic foreign body and a grasper for retrieving the metallic foreign body. As such, in some embodiments, the medical devices disclosed herein are directed to a subset of the general population, including animals, such that, in these embodiments, not all of the general population may benefit from the medical devices. Based on the foregoing, because some of the medical devices of the present disclosure are directed to specific subsets or subclasses of identified individuals (that is, the subset or subclass of individuals "in need" of assistance in addressing one or more specific conditions noted herein), not all individuals will fall within the subset or subclass of individuals as described herein for certain conditions. Individuals in need or subjects in need may be, for example, humans and animals. In particular, individuals in need or subjects in need may be those having a foreign body in a tissue. Foreign bodies may be metal, glass, wood, stone or rock, mineral, and combinations thereof. Foreign bodies may further be, for example, cysts, lumps, neoplastic soft tissue tumors and breast calcifications.

As depicted in FIG. 1, a device 100 for locating and retrieving objects includes a grasper 110 and a probe 130. The grasper 110 may have the shape of a scissor-type handle. The grasper 110 includes a non-movable portion 102 and a movable portion 104. The movable portion 104 is coupled to the non-movable 102 portion, and is movable relative to the non-movable portion 102 to retrieve objects, as described herein. Unlike conventional scissors, hemostats, and other grasping tools in which both portions of the tips move, only the movable portion 104 of grasper 110 moves to grasp objects.

The probe 130 is coupled to the non-movable portion 102 of the grasper 110. Accordingly, when grasping an object, the probe 130 advantageously remains in a fixed position. As depicted in FIG. 1, the movable portion 104 is coupled to the non-movable portion 102 at a first hinge 106 and a second hinge 108, respectively.

More specifically, movable portion 104 includes a handle component 112. The handle component 112 includes an aperture 116 sized and oriented to receive a finger of a user. The non-movable portion 102 includes a corresponding handle component 113 that includes an aperture 118, such that to operate grasper 110, a user inserts a finger into each of apertures 116 and 118, and operates grasper 110 similar to a pair of scissors.

Figure 4:
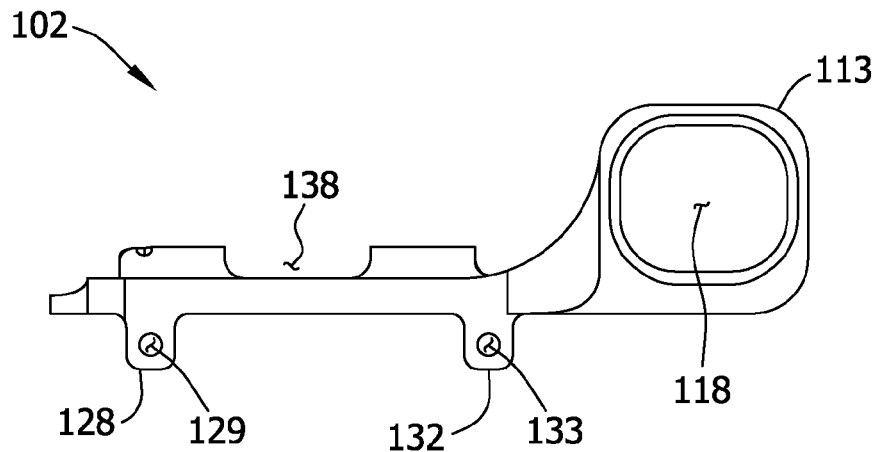
FIG. 4 is a side view of a non-movable portion of the grasper shown in FIG. 1.
Figure 5:
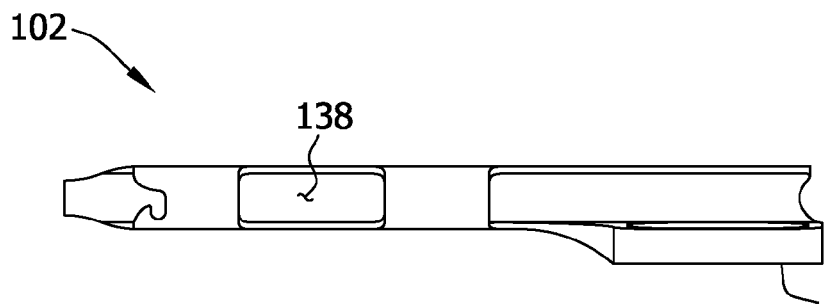
FIG. 5 is a top view of the non-movable portion shown in FIG. 4.
Figure 6:
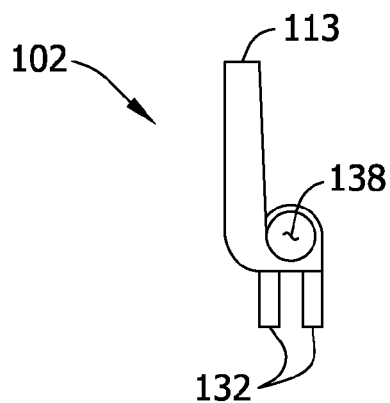
FIG. 6 is an end view of the non-movable portion shown in FIG. 5.
Figure 7:
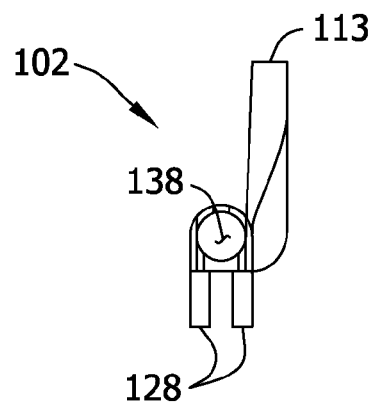
FIG. 7 is an end view of the non-movable portion shown in FIG. 5.
Figure 8:
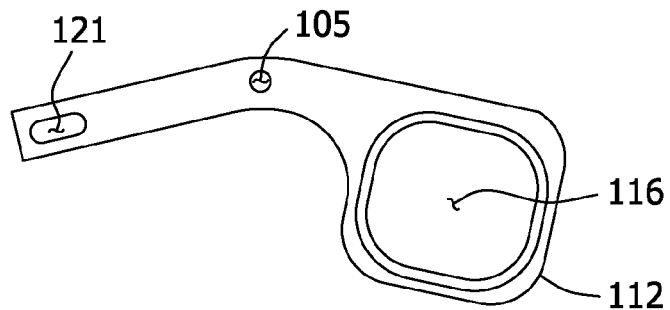
FIG. 8 is a side view of the handle component of the grasper shown in FIG. 1.

Handle component 112 of the movable portion 104 is pivotally coupled to non-movable portion 102 at a first hinge 106. Specifically, as depicted in FIG. 4, non-movable portion 102 includes a first pair of flanges 132 with apertures 133 sized and oriented to receive a fastener 124. As depicted in FIG. 8, handle component 112 of the movable portion 104 includes an aperture 105 sized and oriented to receive the fastener 124. Apertures 133 of the first pair of flanges 132 are oriented with aperture 105 of handle component 112 to receive the fastener 124 to form the first hinge 106.

Figure 13:
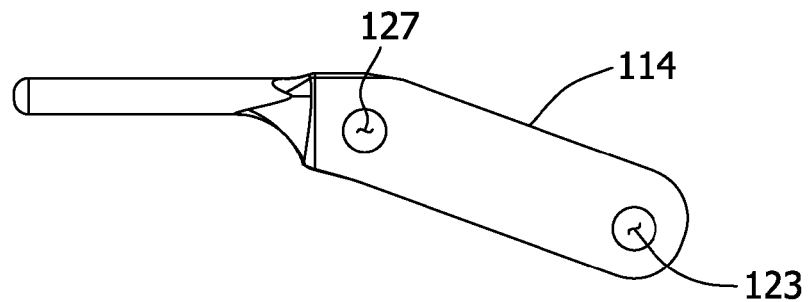
FIG. 13 is a side view of the movable endpiece of movable portion of the handle component shown in FIG. 8.

Movable endpiece 114 of the movable portion 104 includes a grasper tip 136. Movable endpiece 114 is pivotally coupled to non-movable portion 102 at the second hinge 115. As depicted in FIG. 4, non-movable portion 102 includes a second pair of flanges 128 with apertures 129 sized and oriented to receive a fastener 126. As depicted in FIG. 13, movable endpiece 114 of the movable portion 104 includes an aperture 127 sized and oriented to receive the fastener 126 to form the second hinge 115.

Figure 9:
FIG. 9 is a bottom view of the handle component shown in FIG. 8.
Figure 10:
FIG. 10 is a top view of the handle component shown in FIG. 8.
Figure 11:
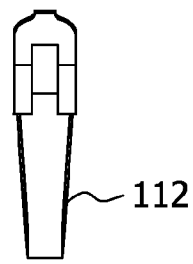
FIG. 11 is an end view of the movable portion of the handle component shown in FIG. 8.
Figure 12:
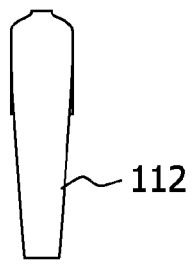
FIG. 12 is an end view of the movable portion of the handle component shown in FIG. 8.

As depicted in FIG. 1, handle component 112 of the movable portion 104 is coupled to movable endpiece 114 at a third hinge 108. As depicted in FIG. 8, handle component 112 includes an aperture 116 for a user's digit, an aperture 105 sized and oriented to receive a first fastener 124, and elongated slots 121. FIG. 9 is a bottom view of the handle component 112 shown in FIG. 8. FIG. 10 is a top view of the handle component 112 shown in FIG. 8. FIG. 11 is an end view of the movable portion of the handle component 112 shown in FIG. 8. FIG. 12 is an end view of the movable portion of the handle component 112 shown in FIG. 8. As depicted in FIG. 13, movable endpiece 114 includes aperture 123 sized and oriented to receive the third fastener 122 and aperture 127 sized and oriented to receive the second fastener 126. Orienting the aperture 123 of the movable endpiece 114 with the elongated slots 121 of the handle component 112 and fastening with the fastener 122 forms the third hinge 108. When handle component 112 is pivoted about the first hinge 106 (e.g., by a user using aperture 116), fastener 122 slides along elongated slots 121 to cause tip portion 136 to pivot about third hinge 108. Accordingly, by operating handle component 112 of movable portion 104, grasper tip 136 can be moved towards and/or away from proximal tip 134 of non-movable portion 102.

Hinges 106, 115, and 108 allow the movable portion 104 to pivot or rotate such that the grasper tip 136 of the movable portion 104 may move relative to the proximal tip 134 of the non-movable portion 102 to allow for grasping an object. While fasteners shown as pins and apertures are used in the embodiment shown in FIG. 1, any fastener known to those skilled in the art may be used to couple non-movable portion 102 to movable portion 104. Suitable fasteners may be, for example, press fit pins, screws, posts and combinations thereof.

The non-movable portion 102 also includes a guide channel 138 for coupling the grasper 110 to the probe 130. In the embodiment depicted in FIGS. 1 and 4-7, the guide channel 138 is a cylindrical channel that extends along the length of non-movable portion 102. Alternatively, the guide channel 138 may have any shape that enables it to receive the probe 130 therein. Advantageously, the probe 130 is slideable in the guide channel 138 along the length of the non-movable portion 102 to allow grasper tip 136 of the grasper 110 to be positioned distal to a proximal tip 134 of the probe 130 when the location of the object is being determined. Accordingly, once the object is located, the grasper 110 may be slid along the length of the probe 130 such that grasper tip 136 of the grasper 110 is positioned proximate to the proximal tip 134 of the probe 130. Thus, the probe 130 also functions as a guide for positioning the grasper 110. When grasper tip 136 of the grasper 110 and proximate tip 134 of the probe 130 are positioned proximate to each other, the object may be grasped. Once grasped, the object may be retrieved from the medium by withdrawing the device from the medium.

Figure 24:
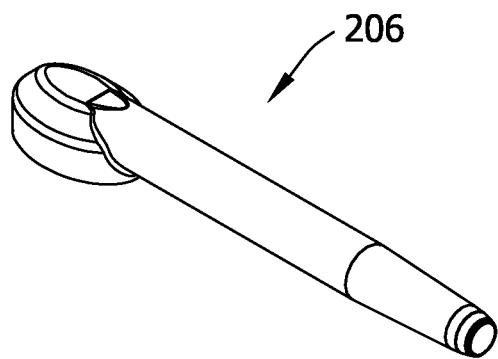
FIG. 24 is a perspective view of a grasper tip in the shape of a cup as shown in FIG. 32.
Figure 25:
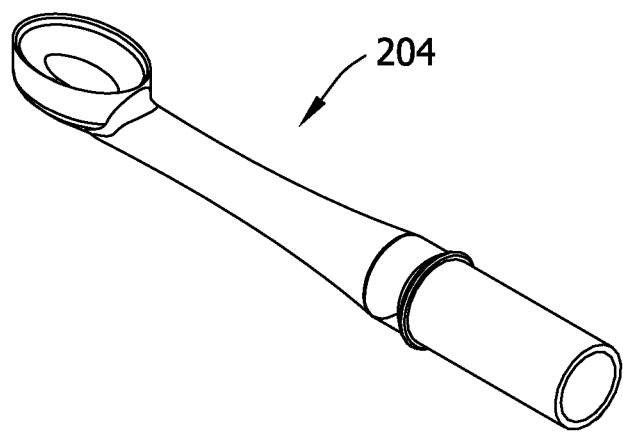
FIG. 25 is a perspective view of a probe tip in the shape of a cup as shown in FIG. 32.
Figure 26:
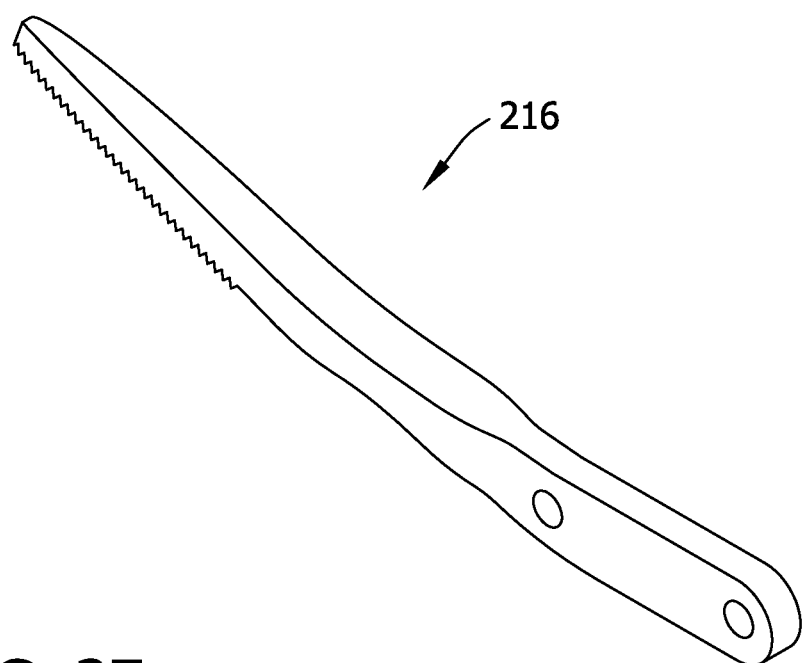
FIG. 26 is a perspective view of a grasper tip in the shape of a forceps with teeth.
Figure 27:
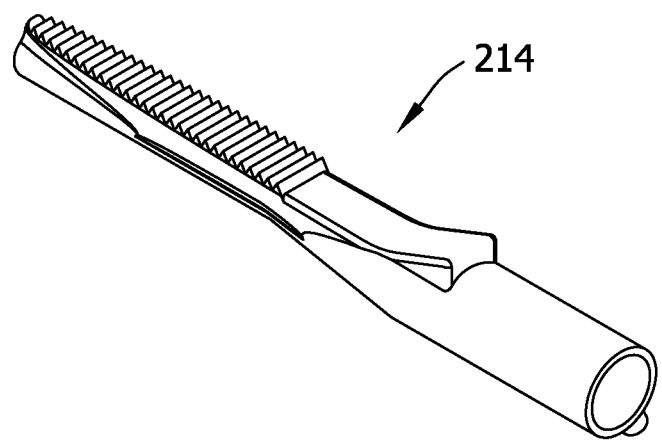
FIG. 27 is a perspective view of a probe tip in the shape of a forceps with teeth.
Figure 28:
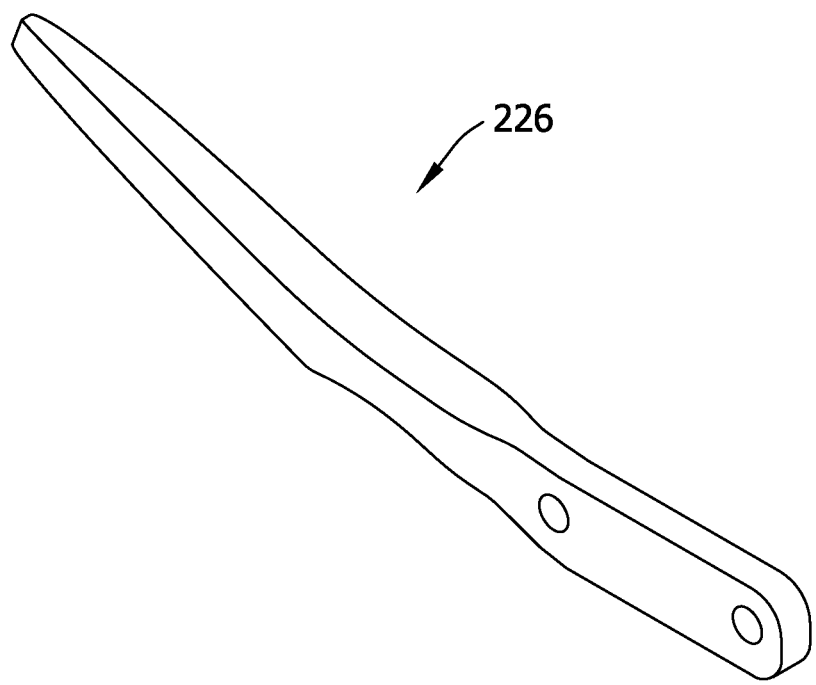
FIG. 28 is a perspective view of a grasper tip in the shape of a forceps without teeth.
Figure 29:
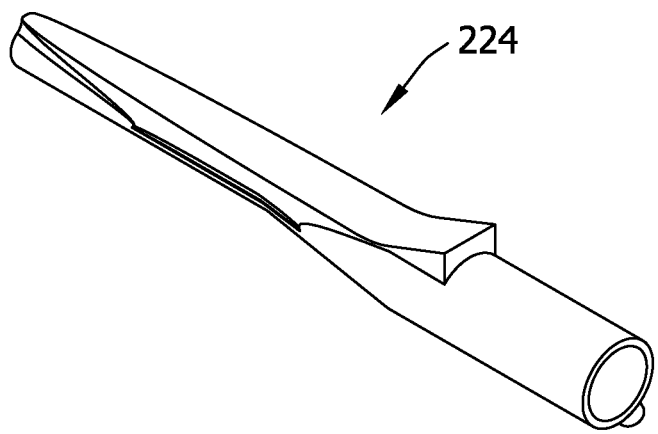
FIG. 29 is a perspective view of a probe tip in the shape of a forceps without teeth.
Figure 30:
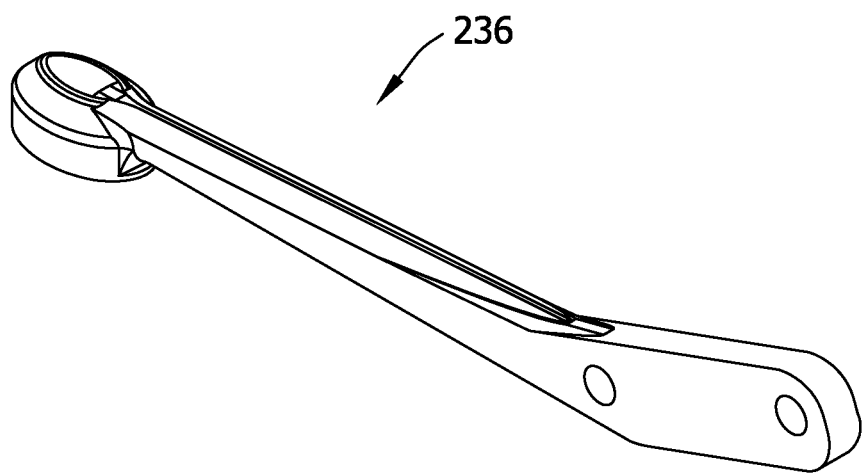
FIG. 30 is a perspective view of a grasper tip in the shape of a cup.
Figure 31:
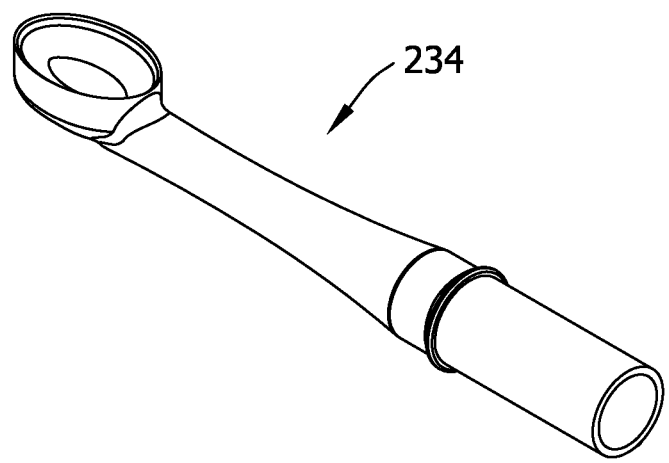
FIG. 31 is a perspective view of a probe tip in the shape of a cup.
Figure 32:
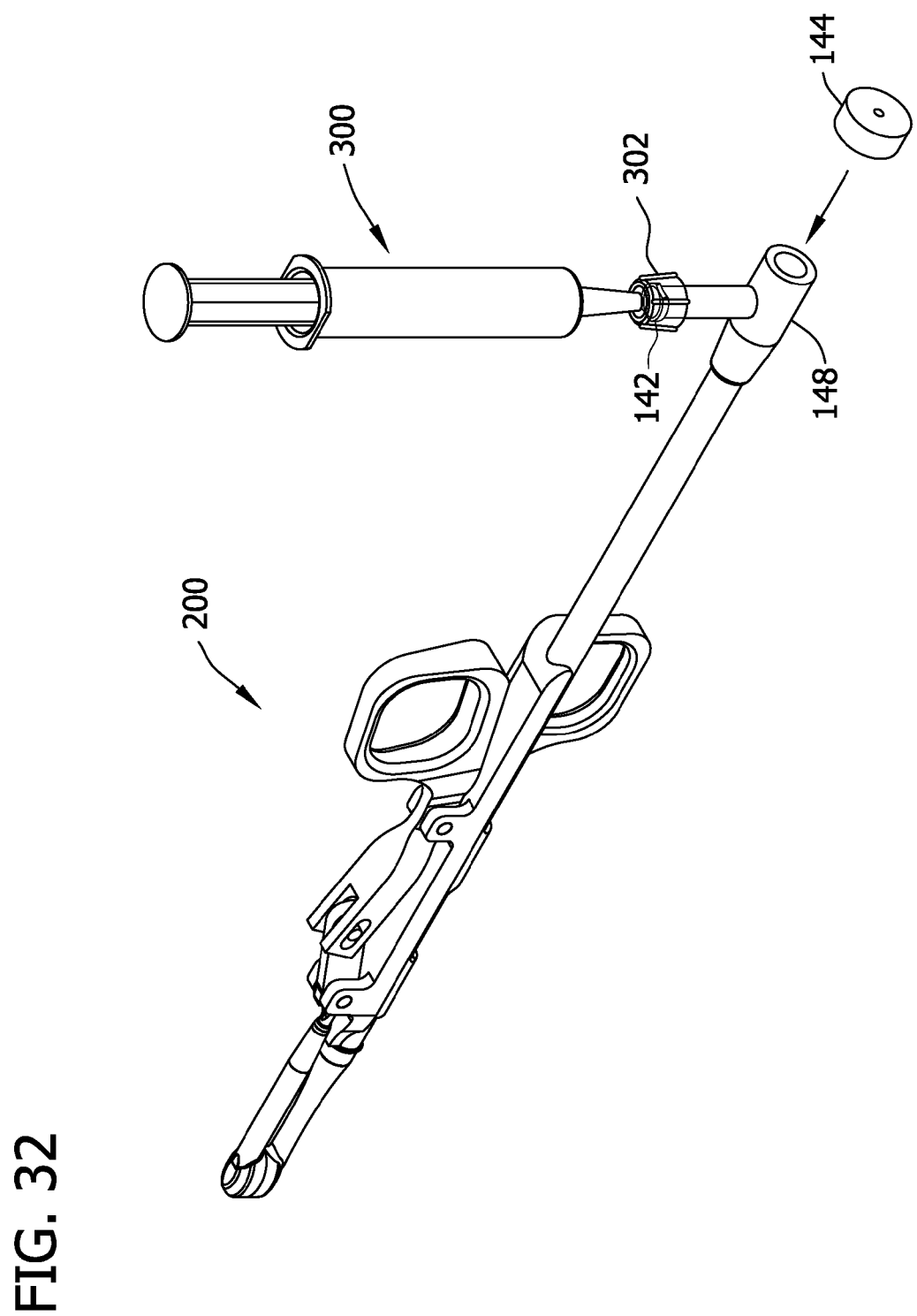
FIG. 32 is a perspective view a device for locating and retrieving an object according to one embodiment of the present disclosure having a grasper tip and a probe tip in the shape of a cup and further showing a syringe coupled to the stopcock end by a fluid fitting.

The grasper tip 136 may be in a variety of shapes as described herein below. The shape of the grasper tip 136 will depend on the type and size of object to be retrieved and the type of medium. The proximate tip 134 of the probe 130 and the grasper tip 136 of the grasper 110 may have the same shape or have different shapes. The proximal tip 134 of the probe 130 and the grasper tip 136 of the grasper 110 may be adapted to accommodate different tip shapes. Suitable tip shapes may be, for example, forceps, scissors, clamps, cups, cup-shaped with at least one aperture, cup biopsy forceps, bladed (e.g., a scalpel blade) and combinations thereof. The tips may further have a smooth surface, a surface with at least one tooth, solid or have an aperture, curved, straight or angled, and any combination thereof. As depicted in FIG. 1, the shape of grasper tip 136 is in the form of a forcep. As depicted in FIG. 24, the grasper tip 206 may be in the form of a cup. As depicted in FIG. 25, the proximal tip 204 may be in the form of a cup. As depicted in FIG. 26, the grasper tip 216 may be in the form of a forceps having teeth. As depicted in FIG. 27, the proximal tip 214 may be in the form of a forceps having teeth. As depicted in FIG. 28, the grasper tip 226 may be in the form of a forceps having a smooth surface. As depicted in FIG. 29, the proximal tip 224 may be in the form of a forceps having a smooth surface. As depicted in FIG. 30, the grasper tip 236 may be in the form of a cup-shape. As depicted in FIG. 31, the proximal tip 234 may be in the form of a cup-shape.

The tip component 120 of the device 100 includes a grasper tip 136 of the grasper 110 and a proximate tip 134 of the probe 130. One or both of the proximate tip 134 and grasper tip 136 may be removable or detachable. In some embodiments, the grasper tip 136 may be interchangeable or removable from movable endpiece 114. In some embodiments, the proximate tip 134 of the shaft 146 of the probe 130 may be interchangeable or removable. Thus, various tips may be attached depending on the object to be retrieved. Tips may be coupled to the device in any manner that enables the device to function as described herein. For example, tips may be screwed onto the device, pressed onto the device, strap fastened, and combinations thereof. In other embodiments the grasper tip 136 and/or the proximal tip 134 may be non-removable. Thus, the grasper tip may be formed as part of the movable endpiece 114 (see e.g., forcep-shaped grasper tip 226 as depicted in FIG. 28 and cup-shaped grasper tip 236 of FIG. 30). Similarly, the proximal tip 134 of the shaft 146 of the probe 130 may be formed as part of the shaft 146. The grasper tip 216 as depicted in FIG. 26 and the proximal tip 214 as depicted in FIG. 27 may include teeth. In other embodiments, the grasper tip 226 as depicted in FIG. 28 and/or the proximal tip 224 as depicted in FIG. 29 may be smooth.

Figure 3:
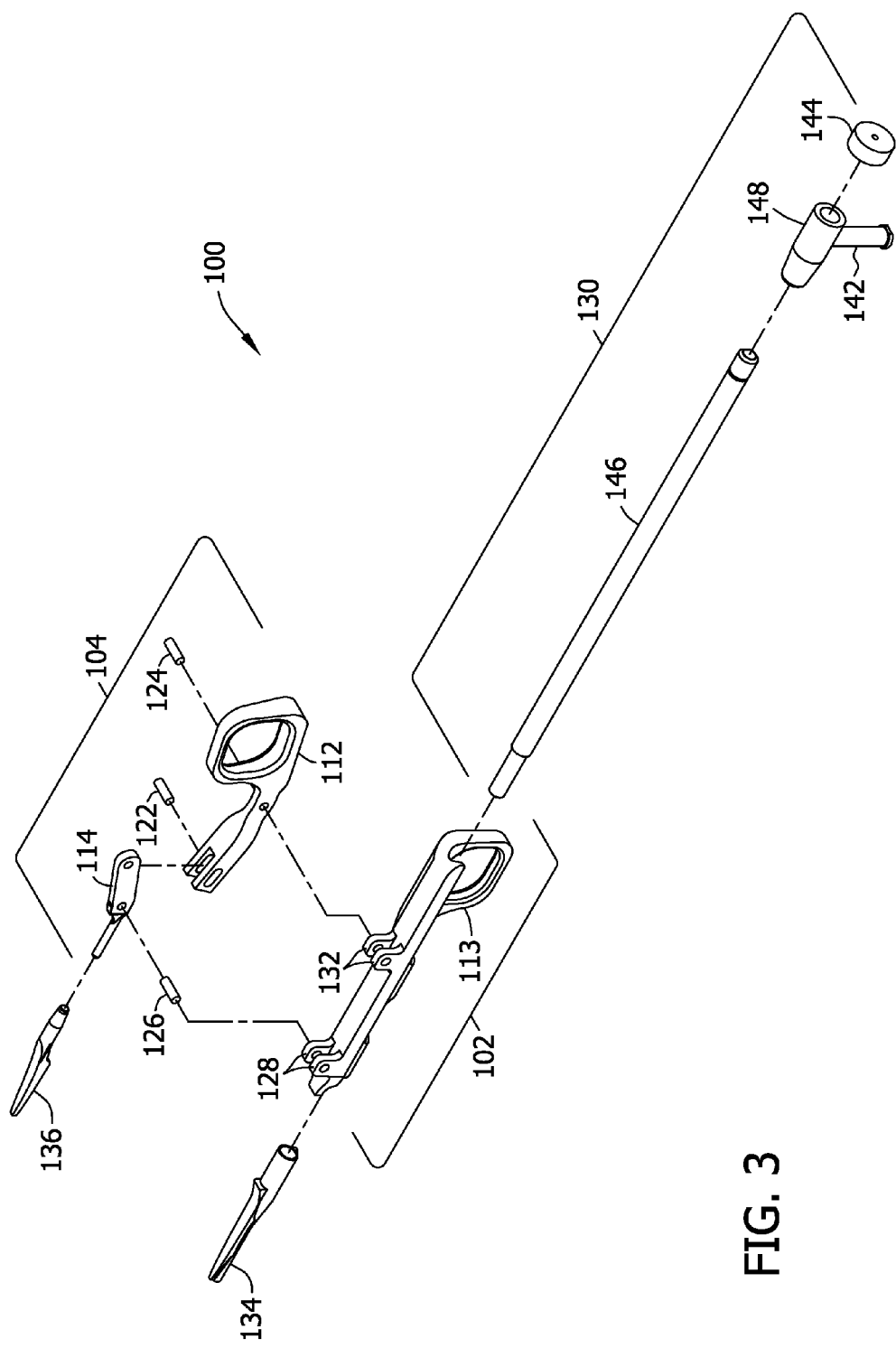
FIG. 3 is an exploded perspective view of the device shown in FIG. 1.
Figure 14:
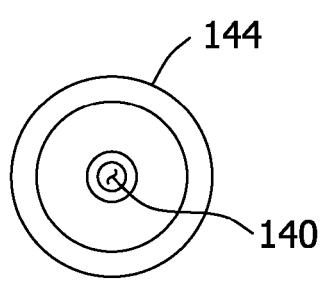
FIG. 14 is an end view of the interior of the stopper of the probe shown in FIG. 1.
Figure 15:
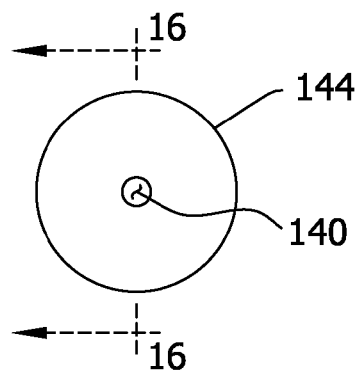
FIG. 15 is an end view of the stopper of the probe shown in FIG. 1.
Figure 16:
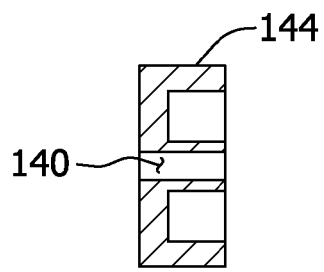
FIG. 16 is a cross-sectional view of the stopper shown in FIG. 15 taken along line 16-16.
Figure 17:
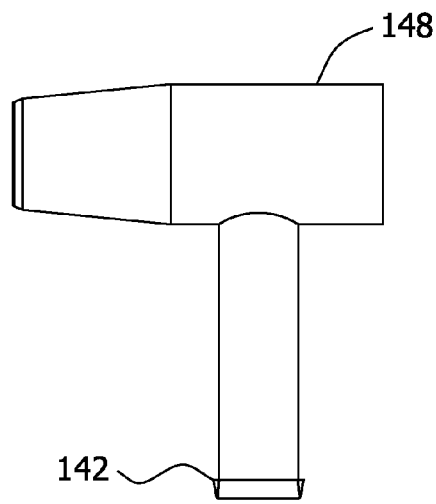
FIG. 17 is a side view of a stopcock end with a fluid fitting shown in FIG. 1.
Figure 18:
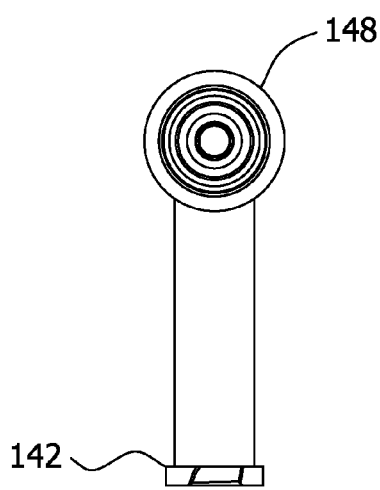
FIG. 18 is an end view of the interior of the stopcock end shown in FIG. 17.
Figure 19:
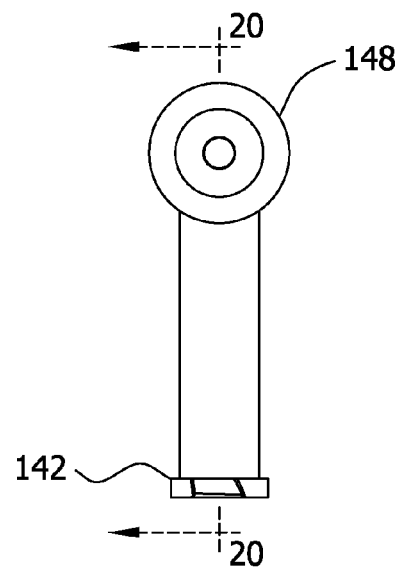
FIG. 19 is an end view of the stopcock end shown in FIG. 17.
Figure 20:
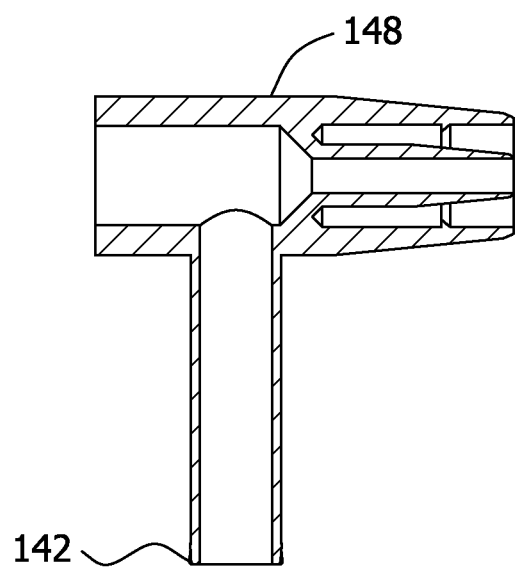
FIG. 20 is a cross-sectional view of the stopcock end shown in FIG. 19 taken along line 20-20.
Figure 22:
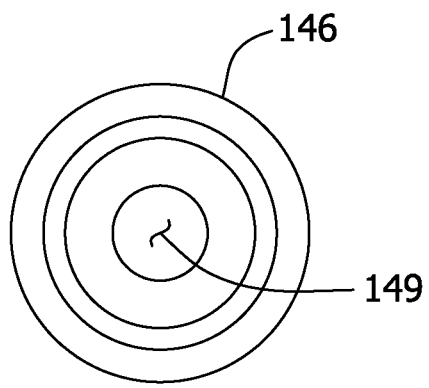
FIG. 22 is an end view of the stopper/stopcock of the probe shown in FIG. 21.
Figure 23:
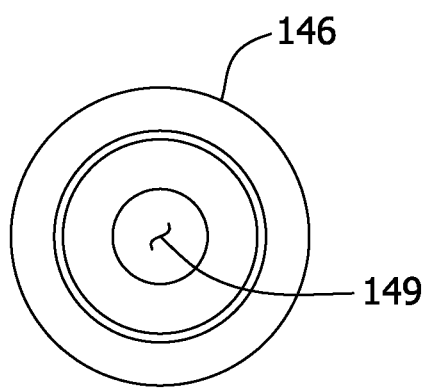
FIG. 23 is an end view of the proximate tip of the probe shown in FIG. 21

The device 100 also includes a probe 130 for locating an object. As depicted in FIG. 3, the probe 130 includes a stopper 144, optionally a stopcock end 138 (optionally having a fluid fitting 142) and a shaft 146. FIG. 14 depicts an interior view of stopper 144 showing aperture 140. FIG. 15, depicts an exterior view of stopper 144 showing aperture 140. FIG. 16 depicts a section through stopper 144 at references 16 of FIG. 15 showing aperture 140. As depicted in FIG. 22, shaft 146 has a distal end 162 to which the stopper 144 and/or stopcock end 148 are coupled. As depicted in FIG. 23, shaft 146 has a proximal end 160 to which the proximal tip 134 is coupled. In other embodiments, the probe 130 is manufactured with a non-detachable proximal tip. As described herein, in one aspect, the probe 130 includes an electronic ultrasound detector for locating an object. In another aspect, the probe 130 includes an electromagnetic detector for locating a metallic object.

Figure 21:
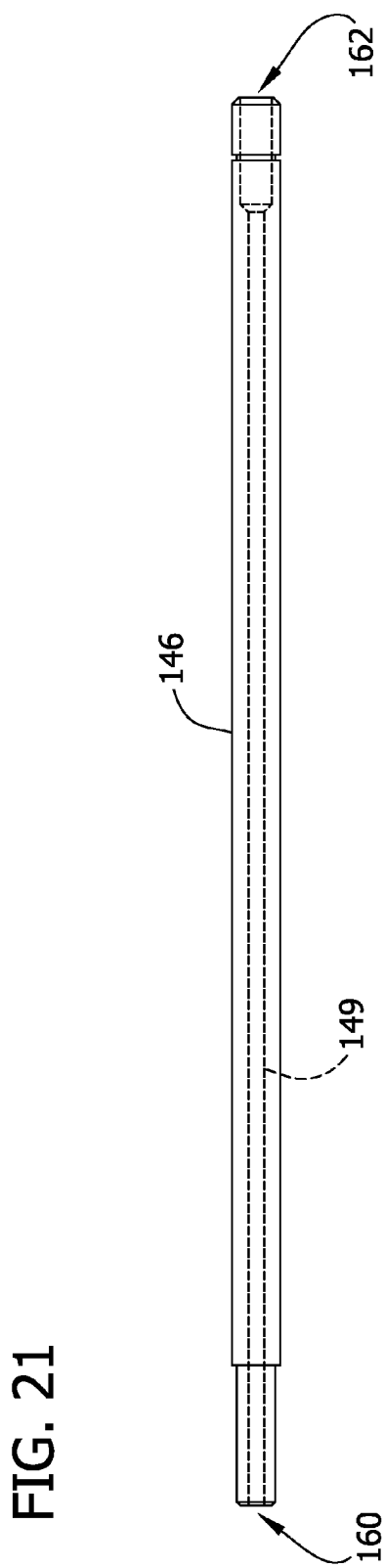
FIG. 21 is a side view of the probe shown in FIG. 1.

The probe 130 includes a bore 149 (see, FIGS. 21-23) through which the detector 152 is inserted. The detector 152 is inserted into the probe 130 through the distal end 162 (see, FIGS. 21 and 22) of the shaft 146 of the probe 130 and positioned at the proximal end 160 (see, FIGS. 21 and 23) of the probe 130. The detector 152 is fed or threaded through the bore 149 of the shaft 146 of the probe 130 to the proximal end 160. Positioning the detector 152 at the proximal end 160 of the probe 130 allows for the directional detection of the object in the medium. The probe 130 may further include a fluid conduit defined therethrough. In one embodiment, the bore 149 through which the detector 152 is fed may serve as the fluid conduit. In another embodiment, the bore and fluid conduit may be separate. A fluid may be supplied to the subject by at least one aperture at the proximal tip 134 of the probe 130. In some embodiments, the devices of the present disclosure may further include a liquid dispenser adapted to supply a liquid through the probe. Any suitable liquid may be supplied through the probe to the medium such as, for example, saline solution, blood, plasma, platelet rich plasma, water, and combinations thereof.

The proximal tip 134 of the probe 130 may be in a variety of shapes as described herein. The shape of the proximal tip 134 will depend on the type and size of object to be retrieved and the type of medium. The proximal tip 134 of the probe 130 may be the same shape or a different shape as the grasper tip 136 of the grasper 110.

The distal end 162 of the probe 130 may be adapted to receive a stopper 144 (FIG. 1). The stopper 144 may include an aperture 140 through which the detector 152 is inserted (see also, FIGS. 14-16). The stopper 144 and the detector 152 form a seal to prevent irrigation fluid from escaping or leaking out of the distal end 162 of the probe 130. The stopper 144 may also block or prevent entry of objects into probe 130 prior to inserting the detector.

In some embodiments, the distal end 162 of the probe 130 may be adapted to receive a stopcock end 148. As depicted in FIGS. 1, 17-20 and 32, the stopcock end 148 may be further adapted to receive a fluid fitting 142 to receive a syringe 300 (as depicted in the device 200 illustrated in FIG. 32) or tubing to allow for irrigation of the medium with a fluid. Any suitable fluid fitting design known by those skilled in the art may be suitable to make secure leak-proof unions 302. Particularly suitable fluid fitting systems may be, for example, a Luer lock fitting (Luer taper fitting), a compression fitting, and combinations thereof. The Luer lock type fluid fitting may be, for example, a LUER-LOK® and a LUER-SLIP® fitting.

In some embodiments, display 158 interface options may be used to notify the user when an object is located with the probe 130. Suitable display interface options may be, for example, visual display interface options, auditory display interface options and combinations thereof. Suitable visual display interface options may be, for example, light indicators, LED indicators, image processing, word processing, numeral, and combinations thereof. Suitable auditory display interface options may be sounds such as, for example, alarms, beeps, voices, and combinations thereof.

Devices of the present disclosure may be manufactured from any suitable material known by those skilled in the art. Different portions of the device may be manufactured from the same material or different materials. For example, the grasper of the device may be manufactured from steel, whereas the probe may be manufactured from plastic. Alternatively, for example, both the grasper and the probe may be manufactured from plastic.

Suitable materials may be, for example, metals, plastics, and combinations thereof. Particularly suitable materials for manufacturing the devices may be biocompatible. Suitable materials for use with an ultrasound detector should preferably be low to ultrasound translucent. Suitable materials for use with an electromagnetic detector should preferably be non-metallic. Particularly suitable materials for manufacturing the instrument may be, for example, thermoplastics such as, for example, polycarbonate-ISO, ABS-M30i, polyphenylsulfone, metals such as, for example, steel, stainless steel, and aluminum, and combinations thereof.

Devices of the present disclosure may be disposable (i.e., single-use) or reusable (i.e., multiple use). Reusable devices may be sterilized, washed, and otherwise cleaned to allow for reuse.

Figure 2:
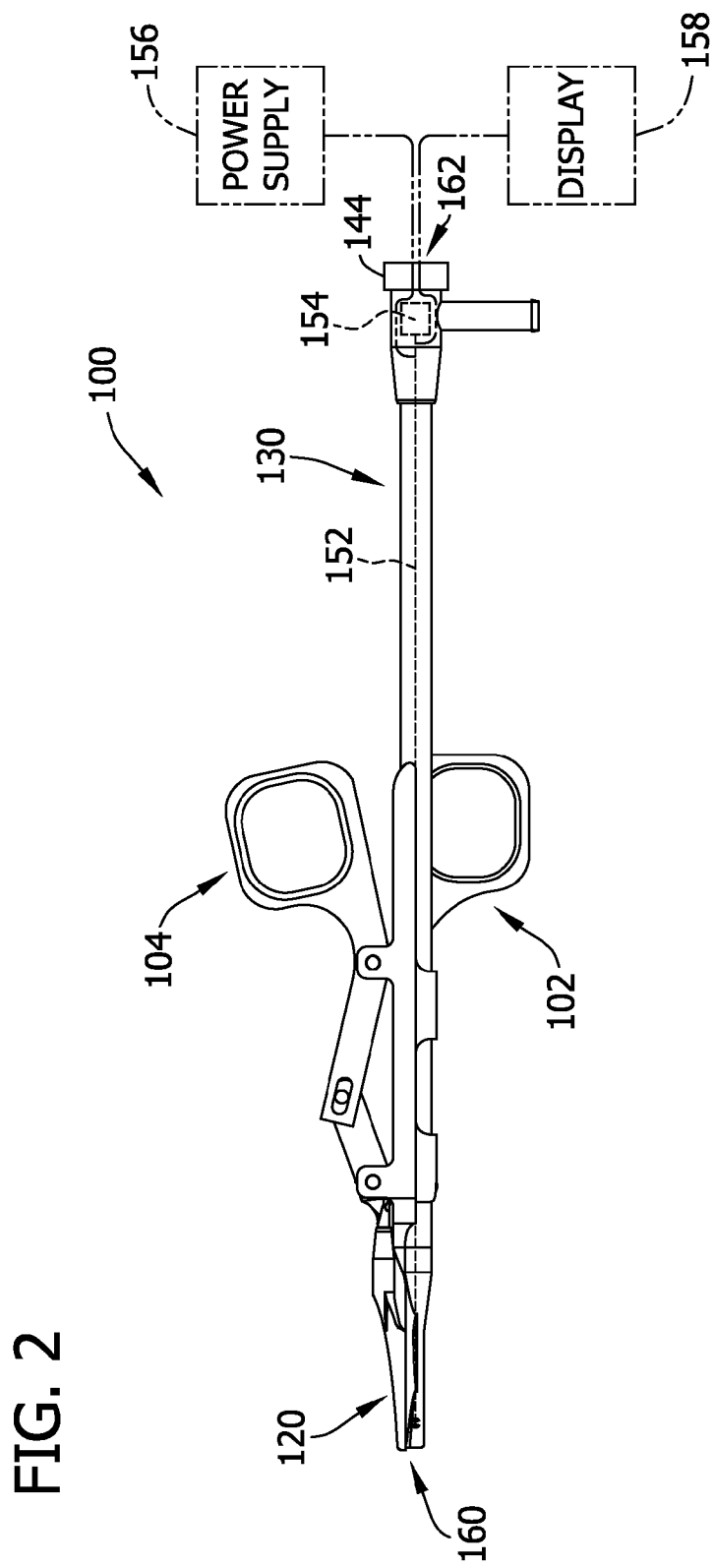
FIG. 2 is a side view of the device shown in FIG. 1.

Devices of the present disclosure may further include electrical components in communication with the detector and wiring that connects the electrical components to an external power supply 156 and display 158 (see, FIG. 2). In some embodiments, the device may be in wireless communication with the display 158. In other embodiments, the power supply may be a battery 154.

The devices of the present disclosure may be used to locate and retrieve any object. Suitable objects may be, for example, metal objects, glass objects, plastic objects, wooden objects, and stone or mineral objects. Metal objects may be, for example, needles, bullets, nails, pellets, and shot. Wooden objects may be, for example, splinters and wood chips. Stone or mineral objects may be, for example, pebbles, stone or rock chips, and grit. A particularly suitable mineral may be, for example, breast tissue calcifications.

A particularly suitable use of the devices including a probe having an ultrasound detector may be as a biopsy clamp/forceps for biopsying a tissue. For example, the devices of the present disclosure are particularly suitable as a medical instrument for locating and biopsying foreign bodies such as, for example, cysts, lumps, neoplastic soft tissue tumors and breast calcifications in soft tissues. The probe having the ultrasound detector may, for example, be inserted into a soft tissue to directionally locate a foreign body in the soft tissue in real time. The ultrasound detector is capable of detecting the differences in densities between the foreign body and the soft tissue. Synergistic with external imaging the foreign body by X-ray or ultrasound and then approximating the depth of the foreign body in the soft tissue based on the two-dimensional X-ray or ultrasound image, the device of the present disclosure including a probe having the ultrasound detector advantageously is capable of directionally locating the foreign body in three-dimensions. Upon locating the foreign body, the probe may be further positioned proximate to the foreign body to position the grasper of the device proximate to the foreign body. The grasper may then be operated as described herein to biopsy the foreign body. In this manner, foreign bodies such as, for example, cysts, lumps, neoplastic soft tissue tumors and breast calcifications in soft tissues may be retrieved from the soft tissue. Once retrieved, the foreign body may be subjected to further processing such as, for example, pathology, testing, and combinations thereof.

The disclosure will be more fully understood upon consideration of the following non-limiting Examples.

EXAMPLES

Example 1

In this Example, an ultrasound was inserted into a probe manufactured from plastic to determine whether ultrasound can image through a probe manufactured using a plastic material.

Specifically, an ultrasound was placed within a plastic probe prototype. A cup of water was used as the test medium. A metal sewing needle was placed into the cup of water as the object to be detected. The prototype plastic probe with the ultrasound was placed into the cup of water near the sewing needle. The needle was detected by the ultrasound, which was transmitting and receiving signals through the plastic probe prototype. Thus, the ultrasound was able to detect a needle in a water medium.

Example 2

In this Example, a probe having an ultrasound detector was used to locate an object in a test medium.

Specifically, a needle was inserted into a bowl of gelatin (JELL-O®) as test media. The probe was then inserted into the test medium. The probe successfully located the needle in the test media.

Example 3

In this Example, a device having a probe housing an ultrasound detector and a grasper was used to locate and retrieve an object in a test medium. Additionally, detection of the object was determined with the ultrasound detector either contained within the tip of the probe or extended outside the tip of the probe to determine whether the material used to manufacture the probe interfered with locating the object.

Specifically, objects made of steel (i.e., a needle), wood (i.e., a splinter), glass, and graphite were inserted into a bowl of gelatin (JELL-O®) as test media. The probe was inserted into the media to locate the object. In one test, the ultrasound detector remained inside the probe tip. In another test, the ultrasound detector was extended through an aperture in the probe tip to a position just outside the probe tip. Once the object was located, the grasper was slid down the probe and positioned near the object. The object was then grasped and removed from the test medium. These results demonstrated that the device was able to locate and remove objects from the test medium. Although positioning the ultrasound detector to a position just outside the probe tip provided clearer ultrasound images of the object in the test medium due to the avoidance of plastic interface distortion, positioning the ultrasound detector within the probe tip was still effective in locating the objects in the test medium despite plastic interface distortion.

The examples described above demonstrate that the device of the present disclosure offer the ability to both locate and retrieve an object. The devices of the present disclosure provide are uniquely capable of locating the object in three-dimensions in real time and retrieving the object while the user holds the device, and thus, avoids the inherent imprecise detection of locating an object externally, and not in real time, in a scanning area such as, for example, an X-ray room or CAT scanner, followed by retrieving the object in another area such as, for example, an operating room.

In view of the above, it will be seen that the several advantages of the disclosure are achieved and other advantageous results attained. As various changes could be made in the above devices and methods without departing from the scope of the disclosure, it is intended that all matter contained in the above description and shown in the accompanying drawings shall be interpreted as illustrative and not in a limiting sense.

When introducing elements of the present disclosure or the various versions, embodiment(s) or aspects thereof, the articles "a", "an", "the" and "said" are intended to mean that there are one or more of the elements. The terms "comprising", "including" and "having" are intended to be inclusive and mean that there may be additional elements other than the listed elements.

What is claimed is:

1. A device for locating and retrieving an object in a medium comprising:
    a probe comprising:
        an ultrasound detector; and
        a probe tip, wherein the ultrasound detector is positioned proximate to the probe tip; and
    a grasper slidably coupled to the probe and comprising:
        a movable portion; and
        a non-movable portion coupled to the movable portion and comprising a grasper tip;
    wherein the probe tip and the grasper tip are configured to grasp the object therebetween.

2. The device of claim 1, further comprising at least one distal handle connected to a distal end of the grasper, wherein the distal handle is operable to move the grasper tip relative to the non-movable portion.

3. The device of claim 1, wherein the probe is further adapted to receive a stopcock end.

4. The device of claim 3, wherein the stopcock end is further adapted to receive a fluid fitting.

5. The device of claim 4, wherein the fluid fitting is selected from the group consisting of a Luer lock fitting, a compression fitting, and combinations thereof.

6. The device of claim 1, further comprising a liquid dispenser adapted to supply a liquid through the probe.

7. A device for locating and retrieving a metallic object in a medium comprising:
    a probe comprising:
        an electromagnetic detector; and
        a probe tip, wherein the electromagnetic detector is positioned proximate to the probe tip; and
    a grasper slidably coupled to the probe and comprising:
        a movable portion; and
        a non-movable portion coupled to the movable portion and comprising a grasper tip;

wherein the probe and the grasper tip are configured to grasp the metallic object therebetween.

8. The device of claim 7, further comprising at least one distal handle connected to a distal end of the grasper, wherein the distal handle is operable to move the grasper tip relative to the non-movable portion.

9. The device of claim 7, wherein the probe is further adapted to receive a stopcock end.

10. The device of claim 9, wherein the stopcock end is further adapted to receive a fluid fitting.

11. The device of claim 10, wherein the fluid fitting is selected from the group consisting of a Luer lock fitting, a compression fitting, and combinations thereof.

12. The device of claim 7, further comprising a liquid dispenser adapted to supply a liquid through the probe.

13. A medical device for locating and retrieving a foreign body in a subject in need thereof comprising:
   a probe comprising:
      a detector; and
      a probe tip, wherein the detector is positioned proximate to the probe tip; and
   a grasper slidably coupled to the probe and comprising:
      a movable portion; and
      a non-movable portion coupled to the movable portion and comprising a grasper tip;
   wherein the probe tip and the grasper tip are configured to grasp the foreign body therebetween.

14. The medical device of claim 13, wherein the detector is selected from the group consisting of an ultrasound detector and an electromagnetic detector.

15. The device of claim 13, further comprising at least one distal handle connected to a distal end of the grasper, wherein the distal handle is operable to move the grasper tip relative to the non-movable portion.

16. The device of claim 15, wherein the at least one distal handle is pivoted about a first hinge to cause a third pair of posts to slide along elongated slots to cause the grasper tip to pivot about a second hinge to move the grasper tip relative to the non-movable portion.

17. The device of claim 13, wherein the probe is further adapted to receive a stopcock end.

18. The device of claim 17, wherein the stopcock end is further adapted to receive a fluid fitting.

19. The device of claim 18, wherein the fluid fitting is selected from the group consisting of a Luer lock fitting, a compression fitting, and combinations thereof.

20. The device of claim 13, further comprising a liquid dispenser adapted to supply a liquid through the probe.

* * * * *